(12) United States Patent
Sako et al.

(10) Patent No.: US 9,670,238 B1
(45) Date of Patent: Jun. 6, 2017

(54) 5'-DIBENZYL PHOSPHATES OF 5-AZACYTIDINE OR 2'-DEOXY-5-AZACYTIDINE

(71) Applicant: OHARA PHARMACEUTICAL CO., LTD., Koka-cho, Koka-shi, Shiga (JP)

(72) Inventors: Magoichi Sako, Shiga (JP); Xiong Luo, Shiga (JP)

(73) Assignee: Ohara Pharmaceutical Co., Ltd., Shiga (JP)

( * ) Notice: Subject to any disclaimer, the term of this patent is extended or adjusted under 35 U.S.C. 154(b) by 0 days.

(21) Appl. No.: 15/355,326

(22) Filed: Nov. 18, 2016

Related U.S. Application Data

(63) Continuation of application No. PCT/JP2016/072009, filed on Jul. 27, 2016, which is a continuation of application No. PCT/JP2016/065659, filed on May 27, 2016.

(30) Foreign Application Priority Data

Nov. 27, 2015 (JP) .................. 2015-231390
Apr. 21, 2016 (JP) .................. 2016-085144

(51) Int. Cl.
*A61K 31/706* (2006.01)
*C07H 19/12* (2006.01)
*C07F 9/6558* (2006.01)

(52) U.S. Cl.
CPC .................. *C07F 9/65586* (2013.01)

(58) Field of Classification Search
None
See application file for complete search history.

(56) References Cited

U.S. PATENT DOCUMENTS 3,816,619 A  6/1974 Bergy et al.
7,642,247 B2 * 1/2010 Daifuku ............... C07D 515/22
                                                      514/43

FOREIGN PATENT DOCUMENTS

| DE | 1922702 A1 | 11/1969 | |
|---|---|---|---|
| WO | WO 2009/042766 A1 | 4/2009 | |
| WO | WO 2011/113173 A1 | 9/2011 | |
| WO | WO2011/153374 | * 12/2011 | ............ A61K 31/70 |
| WO | WO 2011/153374 A1 | 12/2011 | |
| WO | WO 2012/166645 A1 | 12/2012 | |

OTHER PUBLICATIONS

Brueckner et al., "Delivery of 5-Azacytidine to Human Cancer Cells by Elaidic Acid Esterification Increases Therapeutic Drug Efficacy," 2010, 9(5):1256-1264.
Chabner et al., "Purification and Properties of Cytidine Deaminase from Normal and Leukemic Granulocytes," The Journal of Clinical Investigation, Mar. 1974, 53:922-931.
Cihak, A., "Biological Effects of 5-Azacytidine in Eukaryotes," Oncology, 1974, 30(5):405-422.
Colin et al., "Synthesis and biological evaluation of some phosphate trimester derivatives of the anti-cancer drug AraC," Nucleic Acids Research, 1989, 17(18):7195-7201.
Fahy et al., "DNA methyltransferase inhibitors in cancer: a chemical and therapeutic patent overview and selected clinical studies," Expert Opinion on Therapeutic Patents, 2012, 22(12):1427-1442.
Kimura et al., "Studies on Nucleosides and Nucleotides, VIII. Preparation and Reactions of Triphenylphosphoranediylnucleosides," Bulletin of the Chemical Society of Japan, 1980, 53(12):3670-3677.
Krawczyk et al., "5-Azacytidine for the treatment of myelodysplastic syndromes," Expert Opinion on Pharmacotherapy, 2013, 14(9):1255-1268.
Navada et al., "Clinical development of demethylating agents in hematology," The Journal of Clinical Investigation, 2014, 124(1):40-46.
Pradere et al., "Synthesis of Nucleoside Phosphate and Phosphonate Prodrugs," Chemical Reviews, 2014, 114:9154-9218.
Prakash et al., "Synthesis and Evaluation of S-Acyl-2-thioethyl Esters of Modified Nucleoside 5'-Monophosphates as Inhibitors of Hepatitis C Virus RNA Replication," Journal of Medicinal Chemistry, 2005, 48(4):1199-1210.
Roboz et al., "International Randomized Phase III Study of Elacytarabine Versus Investigator Choice in Patients with Relapsed/Refractory Acute Myeloid Leukemia," Journal of Clinical Oncology, Jun. 20, 2014, 32(18):1919-1926.
Singh et al., "DNA Methyltransferase-1 Inhibitors as Epigenetic Therapy for Cancer," Current Cancer Drug Targets, 2013, 13(4):379-399.
Starasid® capsule package insert, 2014.
Vidaza® for injection 100 mg package insert, $2^{nd}$ edition, 2012, with English translation.

* cited by examiner

*Primary Examiner* — Eric Olson
(74) *Attorney, Agent, or Firm* — Foley & Lardner LLP

(57) ABSTRACT

The present invention relates to a novel compound represented by formula (1), or salt thereof,

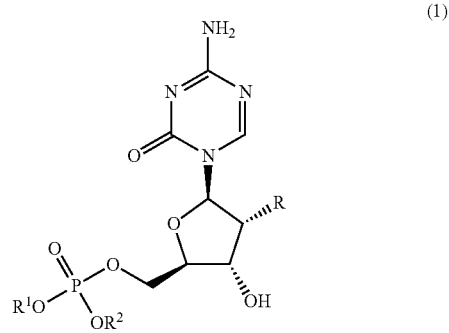

(1)

wherein R is hydroxy group or hydrogen atom; $R^1$ and $R^2$ are the same or different, and are each independently benzyl group which may have a substituent. The present invention provides therapeutically agents, which have remarkable stability against cytidine deaminase, a metabolic enzyme, can be absorbed in vivo by oral administration and inhibit protein synthesis by being incorporated easily into nucleic acid bio-synthesis in vivo for replacing injection agent (5-azacytidine or 2'-deoxy-5-azacytidine) used in clinic for treating myeloma.

11 Claims, No Drawings

5'-DIBENZYL PHOSPHATES OF 5-AZACYTIDINE OR 2'-DEOXY-5-AZACYTIDINE

TECHNICAL FIELD

The present invention relates to novel 5'-dibenzyl phosphate compounds of 5-azacytidine or 2'-deoxy-5-azacytidine which have remarkable stability against cytidine deaminase, a metabolic hydrolyzing enzyme, incorporate easily into nucleic acid bio-synthetic pathway in vivo, and can be used as prodrugs of 5-azacytidine and 2'-deoxy-5-azacytidine which are anti-myeloma agents.

TECHNICAL BACKGROUND

5-Azacytidine (also called as azacytidine or by the product name of Vidaza®) and 2'-deoxy-5-azacytidine (also called as decitabine or by the product name of Dacogen®) have the following chemical structures (i) and (ii), respectively.

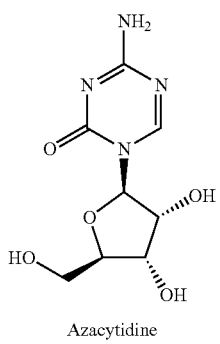

Azacytidine (i)

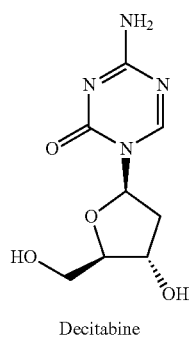

Decitabine (ii)

It has been known that azacytidine and its 2'-deoxy form (also collectively referred to as "azacytidines or 5-azacytidines" in this specification hereafter) inhibit protein synthesis and some enzymes by incorporating into RNA or DNA during nucleic acid bio-synthesis in frequently dividing cells, and show cytotoxicity (patent documents 1 and 2, non patent document 1).

In the field of anti-oncogene promoter, when incorporating into DNA in cells, the azacytidines combine irreversibly with transferase of DNA methyl group relating to 5-methylation of the cytosine ring in highly risky myelodysplastic syndrome in which the formation of a large amount of the 5-methylated cytosine moiety has been confirmed, and cause enzyme inhibition. As a result, they promote the reactivation of anti-oncogenes and accordingly have been clinically used as therapeutic agents showing remarkable effects on highly risky myelodysplastic syndrome (non patent documents 2, 3, and 4).

However, each of these azacytidines can be easily inactivated by cytidine deaminase, a metabolic hydrolyzing enzyme in blood and liver (non patent document 5). As the current clinical situation, they can hardly be used effectively as therapeutic agents for patients with highly risky myelodysplastic syndrome.

As a countermeasure, a 5'-O-elaidic ester of 5-azacytidine, a compound having resistance to cytidine deaminase (development No. CP-4200), was synthesized (patent document 3) and expected to be used as a therapeutic agent for acute leukemia and myelodysplastic syndrome. However, enough progress has not been made with its clinical investigations (non patent documents 6, 7, and 8).

Besides, the same problem has also been pointed out in case of arabinocytidine (also called as Ara-C or cytarabine), an anticancer agent. 5'-O-elaidic ester of Ara-C (also called as elacytarabine, development No.: CP-4055) (non patent document 9) and 5'-chained dialkyl phosphate derivatives of Ara-C (non patent document 10) were synthesized. Furthermore, a 5'-mono higher alkyl phosphate derivative of Ara-C (cytarabine ocphosphate, product name: Starasid® Capsule) (non patent document 11) has already been clinically used as a therapeutic agent for non-lymphocytic acute leukemia in adults and myelodysplastic syndrome.

On the other hand, 5-azacytidyl acids which are 5'-mono phosphoric acids of 5-azacytidines have resistance to cytidine deaminase, a metabolic hydrolyzing enzyme (non patent document 5). However, they are highly polar substances and therefore can hardly pass through cell membrane (non patent document 12), which is considered as a problem.

In addition, a cyclic phosphate derivative of 5-azacytidine has been reported (patent document 4). However, neither its stability against cytidine deaminase nor detailed evaluations on its biological activities has been disclosed.

A 5'-diphosphate of 5-azacytidine has also been reported recently (patent document 5). However, none of its specific chemical structure, stability against cytidine deaminase, or evaluations on its biological activities has been reported.

PRIOR ART DOCUMENTS

Patent Documents

1. Specification of U.S. Pat. No. 3,816,619
2. Specification of DE Pat. No. 1,922,702
3. WO 2009/042766
4. WO 2011/153374
5. WO 2012/166645

Non Patent Documents

1. Oncology, 1974, vol. 30, No. 5, p. 405-422.
2. Expert Opinion on Pharmacotherapy, 2013, vol. 14, No. 9, p. 1255-1268.
3. The Journal of Clinical Investigation, 2014, vol. 124, No. 1, p. 40-46.
4. Package insert of "Vidaza® for Injection 100 mg", 2nd edition, 2012.
5. The Journal of Clinical Investigation, 1974, vol. 53, p. 922-931.
6. Molecular Cancer Therapeutics, 2010, vol. 9, No. 5, p. 1256-1264.
7. Current Cancer Drug Targets, 2013, vol. 13, No. 4, p. 379-399.

8. Expert Opinion, Therapy Patents, 2012, vol. 22, No. 12, p. 1427-1442.
9. Journal of Clinical Oncology, 2014, vol. 32, No. 18, p. 1919-1926.
10. Nucleic Acids Research, 1989, vol. 17, No. 18, p. 7195-7201.
11. Package insert of "Starasid® Capsule", Edition of 2014.
12. Chemical Reviews, 2014, vol. 114, p. 9154-9218.

SUMMARY OF THE INVENTION

Problems to be Solved by the Invention

An object of the present invention is to provide derivatives of 5-azacytidine or 2'-deoxy-5-azacytidine, which have remarkable stability against cytidine deaminase, a metabolic hydrolyzing enzyme, and incorporate easily into the nucleic acid biosynthetic pathway in vivo.

Solutions to the Problem

In order to provide a more useful medicine for treating various myeloma including myelodysplastic syndrome, the present inventors have earnestly undertaken studies on finding novel compounds, which possess both excellent pharmacologic effects and excellent physicochemical properties, have remarkable stability against cytidine deaminase, a metabolic hydrolyzing enzyme, and can incorporate easily into the nucleic acid bio-synthetic pathway in vivo. The present inventors have therefore synthesized a large number of 5'-dialkyl phosphate derivatives of 5-azacytidines and investigated their chemical reactivity. As the result, it has been found out that a 5'-dialkyl phosphate derivative of 5-azacytidines with specific structure unexpectedly shows excellent property as a medicine, which has remarkable stability against cytidine deaminase, a metabolic hydrolyzing enzyme, and incorporates easily into the nucleic acid bio-synthetic pathway in vivo. After further investigation, the present inventors have completed the present invention.

That is, the above problems have been solved by the present invention shown as below.

[1] A compound represented by formula (1), or salt thereof,

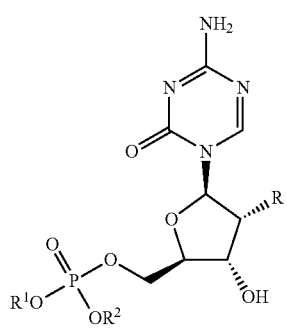

(1)

wherein R is hydroxy group or hydrogen atom; W and $R^2$ are the same or different, and are each independently benzyl group which may have a substituent.

[2] The compound according to that described in [1], wherein W and $R^2$ are each independently benzyl group which may have alkyl group or halogen atom as a substituent.

[3] The compound according to that described in [2], wherein the alkyl group is $C_1$ to $C_6$ alkyl group.

[4] The compound according to that described in [3], wherein the alkyl group is methyl or ethyl.

[5] The compound according to that described in [2], wherein the halogen atom is fluorine atom or chlorine atom.

[6] The compound according to that described in [1], wherein the said $R^1$ and $R^2$ are benzyl group.

[7] A preparation method of the compound according to that described in [1], which includes reacting 5-azacytidine or 2'-deoxy-5-azacytidine with phosphorus oxychloride and then further reacting with benzyl alcohol which may have a substituent, or reacting 5-azacytidine or 2'-deoxy-5-azacytidine with a halogen dibenzyl phosphate derivative which may have a substituent.

[8] A pharmaceutical composition comprising each of the compounds, or salts thereof, according to those described in [1] to [6].

[9] The pharmaceutical composition according to that described in [8], which is a growth inhibitor of myeloma cells.

[10] The pharmaceutical composition according to that described in [8], which is an agent for preventing or treating myeloma including myelodysplastic syndrome.

[11] A method of growth inhibition against myeloma cells in mammals, which includes an administration of each of the compounds, or salts thereof, according to those described in [1] to [6] to mammals in an effective amount.

[12] A method for preventing or treating myeloma including myelodysplastic syndrome in mammals, which includes an administration each of the compounds, or salts thereof, according to those described in [1] to [6] to mammals in an effective amount.

Effects of the Invention

According to the present invention, the 5'-dibenzyl phosphate derivatives of 5-azacytidine, or their 2'-deoxy forms become highly hydrophobic in comparison with their corresponding 5-azacytidyl acids and therefore can be used in oral administration. After being absorbed in intestines, they pass through the membrane of frequently dividing tumor cells without being affected by cytidine deaminase, a hydrolyser in blood or liver before being hydrolyzed non-enzymatically inside cell membrane or cell and free the corresponding 5-azacytidines. Because these 5-azacytidines inhibit protein synthesis and some enzymes by incorporating into RNA and DNA via the nucleic acid bio-synthetic pathway, and show cytotoxicity, they are expected to be used as therapeutic agents for various myeloma including myelodysplastic syndrome.

Modes to Carry Out the Invention

Terms used in the specification and claims have following meanings, unless otherwise stated.

The Compound of the Present Invention, or Salt Thereof

The compound of the present invention is represented by formula (1) as below.

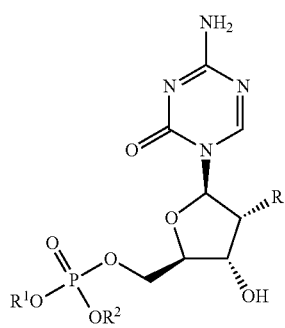

(1)

wherein R is hydroxy group or hydrogen atom; $R^1$ and $R^2$ are the same or different, and are each independently benzyl group which may have a substituent.

"Benzyl group which may have a substituent" means that the benzyl group may have a substituent or may not have a substituent. The number of substituents may be 1 to 5, preferably 1 to 3 at any viable position of benzyl group. When the number of substituents is 2 or more, the substituents may be the same or different. Examples of the substituents include alkyl group, halogen atom, cyano group, nitro group, and the like. Preferable examples include alkyl group and halogen atom.

"Alkyl group" refers to, but is not limited to, a saturated aliphatic hydrocarbon group including $C_1$ to $C_{20}$ straight or branched chains of alkyl group. Representative examples include $C_1$ to $C_6$ alkyl group such as methyl, ethyl, propyl, iso-propyl, butyl, sec-butyl, iso-butyl, tert-butyl, pentyl, hexyl, heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethyl-propyl, octyl, 1-methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-methyloctyl, 7-methyloctyl, 1-ethylheptyl, 1,1-dimethylheptyl, 6,6-dimethylheptyl, decyl, 1-methylnonyl, 2-methylnonyl, 6-methylnonyl, 1-ethyloctyl, 1-propyl heptyl, n-nonyl, n-decyl, and the like, preferably, $C_1$ to $C_6$ alkyl group. Preferable examples of $C_1$ to $C_6$ alkyl group are methyl and ethyl.

"Halogen atom" refers to fluorine atom, chlorine atom, bromine atom, or iodide atom, and the like. Preferable examples are fluorine atom and chlorine atom.

The salts of the compound (1) of the present invention may be any salts as long as they are pharmaceutically acceptable. Their examples include, but are not limited to, acid added salts such as inorganic salts (for example, hydrochloride, sulfate, hydrobromide, phosphate, and the like) and organic salts (for example, acetate, trifluoroacetate, succinate, maleate, fumarate, propionate, citrate, tartrate, lactate, oxalate, methane sulfonate, p-toluene sulfonate, and the like), etc.

The compound (1) of the present invention may be crystal. It can be in single crystalline form or a mixture of multiple crystalline forms. Crystals can be prepared by crystallization according to conventional methods.

In addition, the compound (1) of the present invention may be a solvate (for example, hydrate and the like). Both solvates and non-solvates (for example, non-hydrate and the like) are included in the compound (1).

It has been found out that 5'-dibenzyl phosphate derivatives of 5-azacytidines of the present invention (for example, the compounds A or B of formula (1)) are gradually hydrolyzed in similar environment with physiological conditions (in PBS solution at 37° C.) to generate efficiently corresponding 5-azacytidines. Meanwhile, the said behavior could not be observed in case of 5'-diphenethyl phosphate of 5-azacytidine (compound F) or 5'-diphenyl phosphate of 5-azacytidine (compound G). This was considered as distinctive chemical reactivity of 5'-dibenzyl phosphate derivatives of 5-azacytidine. This finding demonstrates that 5'-dibenzyl phosphate derivatives of 5-azacytidines may possibly become prodrugs of 5-azacytidines.

The stabilities of 5'-dibenzyl phosphate derivatives of 5-azacytidines in the presence of cytidine deaminase have been determined. The results show that each of the derivatives of the present invention is extremely stable against cytidine deaminase. It was confirmed that 5'-dibenzyl phosphate derivatives of 5-azacytidines taken from digestive tract hardly hydrolyze by cytidine deaminase, an enzyme existing in blood or liver. In addition, 5'-dibenzyl phosphate derivatives of 5-azacytidines of the present invention show inhibitory activity against myeloma (for example, growth inhibition against lymphoblastoma cells).

Therefore, 5'-dibenzyl phosphate derivatives of 5-azacytidines of the present invention showing remarkable stability against metabolic hydrolyzing enzyme described above may possibly become prodrugs of therapeutic agents for myeloma.

Preparation Methods of the Compound (1) of the Present Invention

The compound (1) of the present invention can be prepared according to, for example following methods or other similar ones.

Method A

The compound (1), or salt thereof, can be prepared according to conventional methods or other similar ones (referring to Bulletin of the Chemical Society, 1969, 42(12), 3505-8, Nucleic Acids Research, 1984, 12, 5025-36, Chemical & Pharmaceutical Bulletin, 1995, 43(2), 210-215, and WO-2011113173). For example, commercially available 5-azacytidine or 2'-deoxy-5-azacytidine is activated by phosphorus oxychloride in an appropriate solvent and then reacts with benzyl alcohol which may have substituent in the presence of base. As a target compound, a 5'-dibenzyl phosphate of 5-azacytidines (referring to formula (1)) can be obtained.

Method B

The compound (1), or salt thereof, can be prepared by, for example reacting commercially available 5-azacytidine or 2'-deoxy-5-azacytidine with dibenzyl chlorophosphate in an appropriate solvent and in the presence of base. As a target compound, a 5'-dibenzyl phosphate of 5-azacytidines (referring to formula (1)) can be obtained.

(Bases)

The bases used include organic base and inorganic bases. Examples of organic bases include, but are not limited to, triethylamine, N,N-diisopropylethylamine, pyridine, 4-dimethylaminopyridine (DMAP), n-butyl lithium and potassium tert-butoxide. Examples of inorganic bases include, but are not limited to, sodium hydride, sodium carbonate, sodium hydrogen carbonate, potassium carbonate, potassium hydrogen carbonate and cesium carbonate. Amounts of the bases used are preferably more than 2 mol or more of that of the starting material. Furthermore, the range of 2.0 to 50.0 mol based on 1 mol of the starting material; preferably the range of 2.0 to 20.0 mol and more preferably the range of 2.0 to 10.0 mol can be mentioned.

(Solvents)

From the viewpoints of smooth progress of reactions and the like, it is preferred that the reactions of the present invention are carried out in a solvent. Any solvent can be used for the reactions of the present invention as long as the reactions proceed.

Examples of the solvents include, but are not limited to, phosphates such as trimethyl phosphate, triethyl phosphate, tributyl phosphate, triphenyl phosphate, tricresyl phosphate, and the like. The solvents may be used in any amount as long as the reactions proceed. Amounts of solvents for the reactions of the present invention can be adjusted appropriately by a person skilled in the art.

(Reaction Temperature)

Reaction temperature of the present invention is not particularly limited. From the viewpoints of improving yield, by-product control, economic efficiency, and the like, the range of −20 to 50° C. (minus 20 to plus 50° C.), preferable range of −10 to 30° C. (minus 10 to plus 30° C.), more preferable range of −10 to 20° C. (minus 10 to plus 20° C.), even more preferable range of −5 to 15° C. (minus 5 to plus 15° C.), and particularly preferable range of 0 to 10° C. (zero to plus 10° C.) can be mentioned as examples in an embodiment.

(Reaction Time)

Reaction time of the present invention is not particularly limited. From the viewpoints of improving yield, by-product control, economic efficiency, and the like, the range of 0.5 to 120 hours, preferable range of 1 to 72 hours, more preferable range of 1 to 48 hours, even more preferable range of 1 to 24 hours can be mentioned as examples in an embodiment. However, reaction time of the present invention can be adjusted appropriately by a person skilled in the art.

Pharmaceutical Compositions of the Present Invention

The compound (1) of the present invention can be used as a safe medicine for mammals (such as humans, monkeys, cats, pigs, horses, cattle, mice, rats, guinea pigs, dogs, rabbits, and the like) as it is or as a pharmaceutical composition mixed with pharmaceutically acceptable carriers according to conventional methods.

Regarding the said pharmaceutically acceptable carriers, various conventional organic or inorganic substances can be used as formulation materials. Examples include those used in solid formulations, such as excipients, lubricants, binding agents, and disintegrating agents, those used in liquid formulations, such as solvents, solubilizing agents, suspending agents, tonicity agents, buffers, and the like. Furthermore, other formulation additives such as preservative agents, antioxidant agents, coloring agents, sweetening agents, and the like can be used when necessary.

Regarding dosage forms of the pharmaceutical compositions, oral preparations such as tablets, capsules (including soft capsules and microcapsules), granules, powders, syrups, emulsions, suspensions, sustained-release preparations, and the like can be mentioned as examples. These can be administered orally and safely. However, they are not limited to these examples, because liquid formulations can also be administrated.

The pharmaceutical compositions can be prepared according to conventional methods in technical field of formulation. For example, methods described in The Japanese Pharmacopeia, et al. can be applied.

Use of the Compound (1) of the Present Invention

The compound (1) of the present invention can be used in many therapeutic and preventive ways. In a preferable embodiment, the compound (1) of the present invention is used for treatment of extraordinary various diseases which are sensitive to treatment with cytidines (such as decitabine or azacytidine). The preferable symptoms which can be treated with the compound (1) of the present invention also include those accompanying with undesired or uncontrolled cell division, including hematological abnormality, benign tumors, various types of cancers (such as primary and metastatic tumors), restenosis (such as foci in coronary artery, carotid artery and cerebral artery), abnormal stimulation to endothelial cells (atherosclerosis), damage in body tissue caused by surgery, abnormal wound healing, abnormal angiogenesis, diseases causing tissue fibrosis, repetitive dyskinesia, high level angiodysplasia, and productive response followed by organ transplantation.

Regarding hematological abnormality, abnormal proliferation of hemocyte which may cause dysplasia of blood cells and hematological malignant diseases (such as various types of leukemia) are included. As the examples, acute myeloid leukemia, acute promyelocytic leukemia, acute lymphoblastic leukemia, chronic myeloid leukemia, myelodysplasia, and sickle cell anemia can be mentioned. However, they are not limited to these examples.

In several embodiments, hematological abnormality including genetic ones and/or hemoglobinopathy (such as sickle cell anemia) are treated with the compound (1) of the present invention. In some other embodiments, cancers including leukemia, preleukemia, and other myeloma related cancers, such as lung cancer accompanying with myelodysplastic syndrome (MDS), and non-small-cell lung cancer (NSCL) can also be treated with the compound (1) of the present invention. NSCL may include epidermoid cancer or squamous cell cancer, adenocarcinoma, and large carcinoma. MDS may include refractory anemia, refractory anemia having excessive transforming blast cells, and myelomonocytic leukemia.

The pharmaceutical compositions used in the present invention comprise active ingredients in such effective amounts so that the purposes of treating and/or preventing the symptoms (for example, hematological abnormality (such as sickle cell anemia), MDS and/or cancer (for example, NSCL)) can be achieved.

The pharmaceutical compositions used in the present invention are provided as dosage forms for oral administration. The pharmaceutical compositions provided in this specification can be provided in solid, semi-solid, or liquid form for oral administrations, including buccal, lingual, and sublingual ones. Suitable dosage forms for oral administration include tablets, capsules, pills, troches, medical candies, aromatized formulations, cachets, pellets, medicated chewing gum, granules, bulk powders, foaming formulations, non-foaming powders or granules, solutions, emulsions, suspension liquids, solutions, wafers, sprinkles, elixirs, and syrups. However, they are not limited to these examples. In addition to the active ingredient(s), the pharmaceutical compositions may contain binders, fillers, diluents, disintegrants, wetting agents, lubricants, glidants, coloring agents, dye-migration inhibitors, sweetening agents, and flavoring agents. Moreover, they can also contain one or more pharmaceutically acceptable carriers or excipients which are not limited to these examples.

Amounts of the compound (1) in the pharmaceutical compositions or dosage forms of the present invention can be, for example in any one of the ranges of about 1 to 2,000 mg, about 10 to 2,000 mg, about 20 to 2000 mg, about 50 to 1,000 mg, about 100 to 500 mg, about 150 to 500 mg, or about 150 to 250 mg.

When using the compounds of the present invention as anticancer agents, their effective dosages can be properly chosen according to character and stage of cancer, therapeutic strategy, extent of metastasis, amount of tumor, body weight, age, sex, background of genetic race of patients, and the like. Pharmaceutically effective dosages are normally determined according to factors like clinical observation of symptoms, stage of cancer, and the like. Regarding the daily dosage, in case of administration to human, the ranges of about 0.01 to 10 mg/kg (about 0.5 to 500 mg for an adult having body weight of 60 kg), preferably about 0.05 to 5 mg/kg, more preferably about 0.1 to 2 mg/kg can be mentioned as examples. In addition, they may be administered at once or multiple times.

Experimental details about the examples of the compound (1) of the present invention (5'-dibenzyl phosphate derivatives of 5-azacytidines), their stabilities against cytidine deaminase, a metabolic hydrolyzing enzyme and their stabilities in PBS solution as well as their activity of growth inhibition against myeloma cells are shown as below.

EXAMPLES

The examples provided below further illustrate the present invention. It is to be understood that the scope of the present invention is not limited in any way by the scope of the following examples.

In following examples, room temperature refers to about 15 to 30° C. The determinations of $^1$H-NMR and $^{13}$C-NMR were conducted with a JNM-ECZ 400R instrument (JEOL), in which CDCl$_3$, DMSO-d$_6$, or CD$_3$OD was used as a solvent and chemical shifts (δ) from tetramethylsilane, an internal standard, are shown in ppm. Other terms used in the specification have the following meanings. s: singlet; d: doublet; t: triplet; m: multiplet; br: broad; br s: broad singlet; J: constant of J-coupling. In addition, mass determinations of the compounds were conducted with a Yamazen Smart Flash MS system.

Example 1

Activation of 5-Azacytidines by Phosphorus Oxychloride and Subsequent Condensation with Benzyl Alcohols 122 mg of 5-azacytidine was suspended in about 1.0 mL of triethyl phosphate solution. When cooled to 0° C., 93 pt of phosphorus oxychloride (about 2.0 times of 5-azacytidine as the starting material in mol) was added and stirred for about 1 hour. Then, about 0.5 mL (about 5 times in mol) of a corresponding benzyl alcohol and about 0.4 mL (about 9 times in mol) of pyridine were added to the solution and stirred at 0° C. for another 1 hour. The reaction solution was poured into a mixture of ethyl acetate/water and neutralized with a solution of diluted sodium bicarbonate before extracted with ethyl acetate. The extract was washed with saturated saline and dried over anhydrous magnesium sulfate. After insoluble materials were removed by suction, the extract was concentrated to dryness under reduced pressure. The oily residue obtained was separated and purified with a silica gel column (Yamazen Smart Flash MS system) and a 5'-dibenzyl phosphate derivative of 5-azacytidine was obtained as the target compound. This is referred to as synthetic method A hereafter.

Example 2

Condensation of 5-Azacytidines with Dibenzyl Chlorophosphate Derivatives 122 mg of 5-azacytidine was suspended in 1.0 mL of anhydrous pyridine. When cooled to 0° C., about 0.25 mL (about 1.2 times in mol) of a corresponding dibenzyl chlorophosphate derivative was added and stirred for about 1 hour. The reaction solution was poured into a mixture of ethyl acetate/water and neutralized with a solution of diluted sodium bicarbonate before extracted with ethyl acetate. The extract was washed with saturated saline and dried over anhydrous magnesium sulfate. After insoluble materials were removed by suction, the extract was concentrated to dryness under reduced pressure. The oily residue obtained was separated and purified with a silica gel column (Yamazen Smart Flash MS system) and a 5'-dibenzyl phosphate derivative of 5-azacytidine was obtained as the target compound. This is referred to as synthetic method B hereafter.

The separation systems using a silica gel column, separation yields, data obtained from instrumental analysis and partition coefficients of 5'-dibenzyl (or diphenethyl, diphenyl) phosphate derivatives of 5-azacytidines (compounds A to H) which were synthesized according to the methods A and B are shown as below.

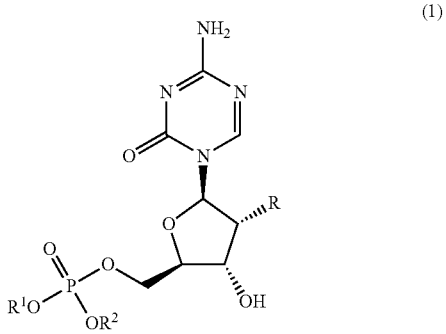

(1)

Compound A) O,O'-dibenzyl 5-azacytidylate (wherein formula (1), R=OH, R$^1$=R$^2$=benzyl): (synthetic method A), Eluting phase for silica gel column: chloroform-methanol, white powder, yield=13%, Mass=505.3 (M$^+$+1): calcd. for C$_{22}$H$_{25}$N$_4$O$_8$P (MW=504.14).

$^1$H-NMR (CDCl$_3$) δ: 8.32 (1H, s), 8.04 (1H, br.), 7.24 (10H, br s), 7.07 (1H, br.), 5.75 (1H, br.), 4.98 and 4.96 (each 2H, each s), 4.83 (1H, br s), and 4.40-4.05 (5H, m) ppm. $^{13}$C-NMR (CDCl$_3$) δ: 165.6, 155.7, 154.5, 137.9, 135.4, 128.6, 128.4, 128.2, 128.0, 127.3, 91.5, 82.2, 74.6, 69.7 (J=4.7 Hz), 69.2, 67.4, and 66.6 ppm.

Partition coefficient, Log P=0.83 (n-octanol/PBS)

Compound B) O,O'-dibenzyl 2'-deoxy-5-azacytidylate (wherein formula (1), R=H, R$^1$=R$^2$=benzyl): (Synthetic method A), Eluting phase of silica gel column: chloroform-methanol, white powder, yield=26%, Mass=489.3 (M$^+$+1): calcd. for C$_{22}$H$_{25}$N$_4$O$_7$P (MW=488.15).

$^1$H-NMR (CD$_3$OD) δ: 8.33 (1H, s), 7.34 (10H, br s), 6.05 (1H, t, J=6.4 Hz), 5.06 and 5.03 (each 2H, each br s), 4.31-4.27 (1H, m), 4.21-4.17 (2H, m), 4.10-4.05 (1H, m), 2.41-2.36 (1H, m), and 2.15-2.06 (1H, m) ppm. $^{13}$C-NMR (CD$_3$OD) δ: 167.7, 156.9, 156.0, 139.5, 137.0 (d, J=6.7 Hz), 129.8, 129.3, 129.2, 128.7, 128.4, 88.2, 86.7 (d, J=7.7 Hz), 71.6, 71.0 (d, J=5.8 Hz), 68.3 (d, J=5.8 Hz), and 41.7 ppm.

Compound C) O,O'-di(4-methyl)benzyl 2'-deoxy-5-azacytidylate (wherein formula (1), R═H, R¹═R²=4-methylbenzyl): (synthetic method A), Eluting phase of silica gel column: chloroform-methanol, white powder, yield=22%, Mass=517.3 (M⁺+1): calcd. for $C_{24}H_{29}N_4O_7P$ (MW=516.18).

¹H-NMR (CD₃OD) δ: 8.31 (1H, s), 7.24-7.15 (8H, m), 6.03 (1H, t, J=6.0 Hz), 5.04 and 4.99 (each 2H, each br s), 4.24-4.22 (1H, m), 4.16-4.10 (2H, m), 4.10-4.05 (1H, m), 2.36-2.32 (1H, m), 2.30 (6H, br s), and 2.06-1.99 (1H, m) ppm. ¹³C-NMR (CD₃OD) δ: 167.3, 156.4, 155.6, 139.4, 138.0, 133.4 (d, J=5.8 Hz), 129.8, 129.4, 128.9, 128.1, 87.7, 86.3 (d, J=7.7 Hz), 71.3, 70.5 (d, J=5.8 Hz), 67.7 (d, J=5.8 Hz), 41.2, and 20.7 ppm.

Compound D) O,O'-di(4-fluoro)benzyl 2'-deoxy-5-azacytidylate (wherein formula (1), R═H, R¹═R²=4-fluorobenzyl): (synthetic method A), Eluting phase of silica gel column: chloroform-methanol, white powder, yield=24%, Mass=525.2 (M⁺+1): calcd. for $C_{22}H_{23}F_2N_4O_7P$ (MW=524.13).

¹H-NMR (CD₃OD) δ: 8.35 (1H, s), 7.39-7.01 (8H, m), 6.07 (1H, t, J=6.4 Hz), 5.06 and 5.03 (each 2H, each br s), 4.33-4.29 (1H, m), 4.28-4.17 (2H, m), 4.10-4.05 (1H, m), 2.45-2.38 (1H, m), and 2.23-2.18 (1H, m) ppm. ¹³C-NMR (CD₃OD) δ: 167.9, 157.1, 156.1, 133.1, 131.6 (d, J=7.7 Hz), 130.5, 116.6, 116.4, 116.1, 116.0, 88.4, 86.8 (d, J=6.8 Hz), 71.6, 70.3 (d, J=5.8 Hz), 68.4 (d, J=5.8 Hz), 67.7, and 41.7 ppm.

Compound E) O,O'-di(4-chloro)benzyl 2'-deoxy-5-azacytidylate (wherein formula (1), R═H, R¹═R²=4-chlorobenzyl): (Synthetic method A), Eluting phase of silica gel column: chloroform-methanol, white powder, yield=20%, Mass=557.1 (M⁺+1): calcd. for $C_{22}H_{23}Cl_2N_4O_7P$ (MW=556.07).

¹H-NMR (CD₃OD) δ: 8.34 (1H, s), 7.33 (8H, br.), 6.07 (1H, t, J=6.4 Hz), 5.06 and 5.04 (each 2H, each br s), 4.35-4.30 (1H, m), 4.28-4.17 (2H, m), 4.12-4.05 (1H, m), 2.45-2.34 (1H, m), and 2.25-2.15 (1H, m) ppm. ¹³C-NMR (CD₃OD) δ: 166.5, 155.8, 154.8, 137.0 (d, J=7.7 Hz), 134.4, 133.1, 129.5, 128.7, 128.6, 128.1, 87.1, 85.4 (d, J=6.8 Hz), 70.2, 68.9 (d, J=5.8 Hz), 67.2 (d, J=5.8 Hz), 66.3, and 40.3 ppm.

Compound F) O,O'-diphenethyl 5-azacytidylate (wherein formula (1), R═OH, R¹═R²=phenethyl) (Synthetic method A), Eluting phase of silica gel column: chloroform-methanol, white powder, yield=16%, Mass=533.3 (M⁺+1): calcd. for $C_{24}H_{29}N_4O_8{}^{13}$ (MW=532.17).

¹H-NMR (CDCl₃) δ: 8.35 (1H, s), 8.05 (1H, br.), 7.26 (1H, s), 7.23-7.12 (10H, m), 5.79 (1H, br.), 4.28 (1H, b s), 4.30-3.89 (4H, m), and 4.15-4.11 & 2.89-2.85 (each 4H, each m) ppm. ¹³C-NMR (CDCl₃) δ: 165.7, 155.7, 154.4, 138.2, 136.9, 129.0, 128.8, 128.6, 128.5, 128.3, 126.9, 126.7, 126.4, 126.2, 91.3, 82.3, 74.8, 69.3, 68.4 (J=5.4 Hz), 66.3, 36.9, and 36.4 (J=7.6 Hz) ppm.

Compound G) O,O'-diphenyl 5-azacytidylate (wherein formula (1), R═OH, R¹═R²=phenyl): (Synthetic method B), Eluting phase of silica gel column: chloroform-methanol, white powder, yield=16%, ¹H-NMR (CDCl₃) δ: 8.28 (1H, s), 7.26 and 7.15 (each 5H, each br s), 5.77 (1H, br s), and 4.6-4.0 (5H, m) ppm. ¹³C-NMR (CDCl₃) δ: 165.6, 155.4, 151.8, 129.8, 129.5, 129.1, 128.9, 128.2, 125.5, 92.4, 82.1, 74.9, 72.5, 69.0, 67.6, and 59.0 ppm.

Compound H) O,O'-diphenyl 2'-deoxy-5-azacytidylate (wherein formula (1), R═H, R¹═R²=phenyl) (Synthetic method B), Eluting phase of silica gel column: chloroform-methanol, white powder, yield=15%, ¹H-NMR (CDCl₃) δ: 8.28 (1H, s), 7.40-7.15 (10H, m), 6.74 (1H, br), 6.13 (1H, br.), 6.11 (1H, dd, J=5.8 and 8.0 Hz), 5.23-5.18 (1H, m), 4.52-4.40 (2H, m), 4.39-4.37 (1H, m), 2.76-2.70 (1H, m), and 2.09-1.97 (1H, m) ppm. ¹³C-NMR (CDCl₃) δ: 165.9, 155.1, 153.2, 150.0 (d, J=4.7 Hz), 129.9, 125.8, 125.7, 119.9 (d, J=4.6 Hz), 86.4, 83.8 (d, J=7.7 Hz), 78.4 (d, J=4.4 Hz), 67.4 (d, J=5.3 Hz), and 39.7 (d, J=5.4 Hz) ppm.

Test Example 1

Stability of 5'-Dibenzyl Phosphate Derivatives of 5-Azacytidines Against Cytidine Deaminase 1 mg each of the 5'-dibenzyl phosphate derivatives of 5-azacytidines (formula (1)) was dissolved in 1 mL of acetonitrile. 10 μL of the solution was diluted with 1 mL of PBS. 10 μL of PBS solution of cytidine deaminase was added and stirred at 37° C. for about 30 minutes to 1 hour. 1 mL of acetonitrile was added to the reaction solution and separated by centrifugation. The supernatant obtained was analyzed with HPLC. As examples, the analytical results of the experiments on O,O'-dibenzyl 5-azacytidylate (wherein formula (1), R═OH, R¹═R²=benzyl) (compound A), O,O'-dibenzyl 2'-deoxy-5-azacytidylate (wherein formula (1), R═H, R¹═R²=benzyl) (compound B), O,O'-di(4-fluoro) benzyl 2'-deoxy-5-azacytidylate (where in formula (1), R═H, R¹═R²=4-fluorobenzyl) (compound D, O,O'-diphenethyl 5-azacytidylate (where in formula (1), R═OH, R¹═R²=phenethyl) (compound F), 5-azacytidine, and 2'-deoxy-5-azacytidine are shown in Table 1.

Cytidine deaminase: CDA (1-146aa), Human, His-tagged, Recombinant cytidine deaminase (ATGen)

HPLC Conditions:

Column: CAPCELL PAK ADME (4.6 mm×150 mm, particle size:3 μm)

Elution: A=Purified water containing 10 mM ammonium formate

B=Acetonitrile

Gradient mode: A:B=99:1→5:95/30 minutes

Flow rate: 1.0 mL/min

Oven temperature: 40° C.

Detection: UV240 nm

TABLE 1

| Starting material | Change in HPLC pattern |
| --- | --- |
| 5-Azacytidine | The peak of the starting material disappeared completely after 30 minutes. |
| 2'-Deoxy-5-azacytidine | The peak of the starting material disappeared completely after 30 minutes. |
| O,O'-dibenzyl 5-azacytidylate (compound A) | Almost no change in the peak of the starting material was confirmed even after 1 hour. |
| O,O'-dibenzyl 2'-deoxy-5-azacytidylate (compound B) | Almost no change in the peak of the starting material was confirmed even after 1 hour. |
| O,O'-di(4-fluoro)benzyl 2'-deoxy-5-azacytidylate (compound D) | Almost no change in the peak of the starting material was confirmed even after 1 hour. |
| O,O'-diphenethyl 5-azacytidylate (compound F) | Almost no change in the peak of the starting material was confirmed even after 1 hour. |

In addition, O,O'-diphenyl 5-azacytidylate (compound G) and O,O'-diphenyl 2'-deoxy-5-azacytidylate (compound H) were also extremely stable under these conditions.

It has been accordingly confirmed that 5'-dibenzyl phosphate derivatives of 5-azacytidines of the present invention are extremely stable against cytidine deaminase. On the other hand, 5-azacytidine 2'-deoxy-5-azacytidine (referring to formula (1)) disappeared completely under the above reaction conditions.

Test Example 2

Non-Enzymatic Hydrolysis Reactivity of 5'-Dibenzyl Phosphate Derivatives of 5-Azacytidines About 1 mg each of the obtained 5'-dibenzyl phosphate derivatives of 5-azacytidines (referring to formula (1)), such as O,O'-dibenzyl 5-azacytidylate (compound A) or O,O'-dibenzyl 2'-deoxy-5-azacytidylate (compound B) was dissolved in 1 mL of acetonitrile. 5 μL of the solution was added to 100 μL of PBS solution (pH7.4 to 7.5) and the solution was stirred at 37° C. The reactions were traced by HPLC analysis. As the results, the productions of 5-azacytidine or 2'-deoxy-5-azacytidine were confirmed gradually.

HPLC conditions were same as those in test example 1.

TABLE 2

| | 5-Azacytidine or 2'-deoxy-5-azacytidine (%) | | |
|---|---|---|---|
| | After 4 hours | After 8 hours | After 24 hours |
| O,O'-dibenzyl 5-azacytidylate (compound A) | 18 | 35 | 67 |
| O,O'-dibenzyl 2'-deoxy-5-azacytidylate (compound B) | 8 | 8 | 45 |

In addition, almost no change was confirmed even after 24 hours in O,O'-diphenethyl 5-azacytidylate (compound F) and O,O'-diphenyl 5-azacytidylate (compound G) which were prepared according to synthetic method A.

Test Example 3

Anti-Myeloma Activity of 5'-Dibenzyl Phosphate Derivatives of 5-Azacytidines

To the solutions containing about 4000 myeloma cells (RPMI-8226), solutions of 5'-dibenzyl phosphate derivatives of 5-azacytidines at concentrations of 0.0033 μM, 0.01 μM, 0.033 μM, 0.1 μM, 0.33 μM, 1 μM, 3.3 μM, 10 μM, 33 μM, or 100 μM were added. After incubation in RPMI-1640 (containing 10% FBS and 1% Penn-strep) for 72 hours, cell count was determined and the values of $IC_{50}$ were calculated as inhibitory effect against cell proliferation (referring to Journal of Clinical Pathology, 2006, 59, 947-951).

TABLE 3

| Compound | $IC_{50}$ (μM) |
|---|---|
| O,O'-dibenzyl 5-azacytidylate (compound A) | 1.71 |
| O,O'-di(4-fluoro)benzyl 2'-deoxy-5-azacytidylate (compound D) | 0.78 |

TABLE 3-continued

| Compound | $IC_{50}$ (μM) |
|---|---|
| O,O'-diphenyl 5-azacytidylate (compound G) | >100 |
| 2'-Deoxy-5-azacytidine | 0.03 |

INDUSTRIAL APPLICABILITY

According to the present invention, a pharmaceutical preparation can be provided to clinical practice potentially in replacement of 5-azacytidine or 2'-deoxy-5-azacytidine as a therapeutic agent for various kinds of myeloma including myelodysplastic syndrome.

What is claimed is:

1. A Compound represented by formula (1), or salt thereof,

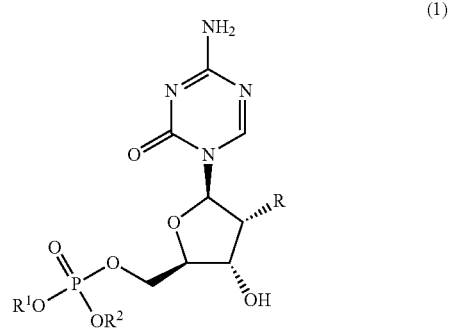

wherein R is hydroxy group or hydrogen atom; $R^1$ and $R^2$ are the same or different, and are each independently benzyl group which may have a substituent.

2. The compound according to claim 1, wherein $R^1$ and $R^2$ are each independently benzyl group which may have alkyl group or halogen atom as a substituent.

3. The compound according to claim 2, wherein the alkyl group as a substituent is $C_1$ to $C_6$ alkyl group.

4. The compound according to claim 3, wherein the alkyl group as a substituent is methyl or ethyl.

5. The compound according to claim 2, wherein the halogen atom as a substituent is fluorine atom or chlorine atom.

6. The compound according to claim 1, wherein the said Wand $R^2$ are benzyl group.

7. The compound according to claim 1, which is O,O'-dibenzyl 5-azacytidylate, O,O'-dibenzyl 2'-deoxy-5-azacytidylate, O,O'-di(4-methyl)benzyl 2'-deoxy-5-azacytidylate, O,O'-di(4-fluoro)benzyl 2'-deoxy-5-azacytidylate or O,O'-di(4-chloro)benzyl 2'-deoxy-5-azacytidylate.

8. A preparation method of the compound according to claim 1, which includes reacting 5-azacytidine or 2'-deoxy-5-azacytidine with phosphorus oxychloride and then further reacting with benzyl alcohol which may have a substituent, or reacting 5-azacytidine or 2'-deoxy-5-azacytidine with a halogen dibenzyl phosphate derivative which may have a substituent

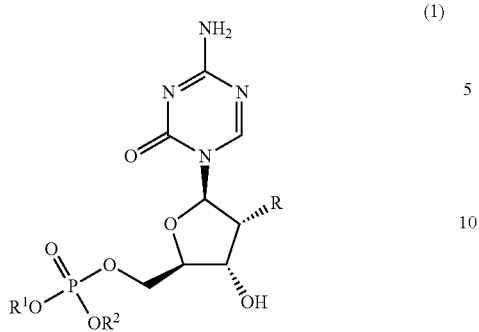
(1)

9. A pharmaceutical composition comprising each of the compounds, or salts thereof, according to claim 1.

10. A method for treatment of diseases which are sensitive to treatment with 5-azacytidine by using the compound or salt thereof of claim 1.

11. A method for treatment of symptoms, which are hematological abnormality, benign tumors, various types of cancers, restenosis, abnormal stimulation to endothelial cells, damage in body tissue caused by surgery, abnormal wound healing, abnormal angiogenesis, diseases causing tissue fibrosis, repetitive dyskinesia, high level angiodysplasia, and productive response followed by organ transplantation by using the compound or salt thereof of claim 1.

* * * * *